United States Patent [19]

Tartaglia

[11] Patent Number: 4,464,173
[45] Date of Patent: Aug. 7, 1984

[54] MEDICAL SYRINGE

[76] Inventor: John A. Tartaglia, 108 Stoddard Rd., Waterbury, Conn. 06708

[21] Appl. No.: 447,775

[22] Filed: Dec. 8, 1982

[51] Int. Cl.³ .............................................. A61M 5/00
[52] U.S. Cl. ..................................................... 604/89
[58] Field of Search ................... 604/89, 90, 191, 218, 604/220, 221, 228

[56] References Cited

U.S. PATENT DOCUMENTS 2,841,145 7/1958 Epps ...................................... 604/89
3,662,753 5/1972 Tassell .................................. 604/89

*Primary Examiner*—John D. Yasko

[57] ABSTRACT

A first hollow elongated cylinder has a first inner diameter. One end of the first cylinder is open. The opposite end of the first cylinder is provided with sealed tip adapted to detachably receive a hypodermic needle. A second hollow elongated cylinder has a second and larger inner diameter. One end of the second cylinder is open. The opposite end of the second cylinder has centered therein a circular port with a diameter equal to the first diameter. The cylinders are disposed end to end along a common cylindrical axis. The opposite end of the second cylinder is secured to the open end of the first cylinder with said port being coincident with the open end of the first cylinder. A sealing disc is centered on said axis and is slidable back and forth in said cylinders along said axis, said disc having a diameter equal to said first diameter and when disposed in said first cylinder engaging the inner surface thereof with a liquid tight seal. A bushing is disposed in the open end of the second cylinder and has a circular opening centered on said axis, said opening having a third diameter smaller than said first diameter. An elongated cylindrical piston extends slidably through said opening, there being a liquid tight seal between said piston and said bushing. One end of said piston is disposed outside of the second cylinder and is enlarged, said piston being aligned with and centered on said axis, the length of the piston being longer than the combined lengths of said first and second cylinders. Cooperating detachably engagable means are on said disc and on the opposite end of the piston whereby said opposite piston end can be detachably secured to said disc.

3 Claims, 3 Drawing Figures

MEDICAL SYRINGE

BACKGROUND OF THE INVENTION

Certain medicines which must be administered to patients by injection consist of lyophilized powder dissolved in a diluent. The powder and diluent must be mixed together immediately before use, since if the powder and diluent are mixed at an earlier time, the medicine will deteriorate rapidly.

Conventionally the powder and diluent are mixed at time of dosage and the medicine is transferred into a syringe for immediate subsequent injection.

The present invention is directed toward a new type of syringe wherein powder and diluent can be stored in separate chambers and can be mixed in the syringe immediately before the same syringe can be used to inject the medicine into the patient.

SUMMARY OF THE INVENTION

A medical syringe in accordance with the invention comprises a first hollow elongated cylinder having a first inner diameter, one end of the first cylinder being open, the opposite end of the first cylinder being closed and provided with sealed means or tip adapted to detachably receive a hypodermic needle.

A second hollow elongated cylinder has a second and larger inner diameter, one end of the second cylinder being open, the opposite end of the second cylinder has centered therein a circular port with a diameter equal to the first diameter. The cylinders are disposed end to end along a common cylindrical axis, the closed end of the second cylinder being secured to the open end of the first cylinder with said port being coincident with the open end of the first cylinder.

A sealing disc is centered on said axis and is slidable back and forth in said cylinders along said axis, said disc having a diameter equal to said first diameter and when disposed in said first cylinder engaging the inner surface thereof with a liquid tight seal.

A bushing is disposed in the open end of the second cylinder and has a circular opening centered on said axis, said opening having a third diameter smaller than said first diameter.

An elongated cylindrical piston extends slidably through said opening, there being a liquid tight seal between said piston and said bushing. One end of said piston is disposed outside of the second cylinder and is enlarged, said piston being aligned with and centered on said axis, the length of the piston being longer than the combined lengths of said first and second cylinders.

Cooperating detachably engagable means are on said disc and on the opposite end of the piston whereby said opposite piston end can be detachably secured to said disc.

The lyophilized powder can be disposed in the first cylinder with the sealing disc spaced from the piston and disposed in the port. The diluent can be disposed in the second cylinder.

In use, the piston is moved until the cooperating means are engaged. The piston is then pulled partially out of the second cylinder to move the disc out of the port into the second cylinder. The diluent then flows out of the second cylinder into the first cylinder to mix with the powder and form the medicine. A hypodermic needle can then be secured to the tip. After the seal in the tip is broken, the syringe can be used to administer the injection as desired.

BRIEF DESCRIPTION OF THE DRAWINGS

FIG. 3 is a view similar to FIG. 2 but showing a modification thereof.

DETAILED DESCRIPTION OF PREFERRED EMBODIMENTS

Figure 1:
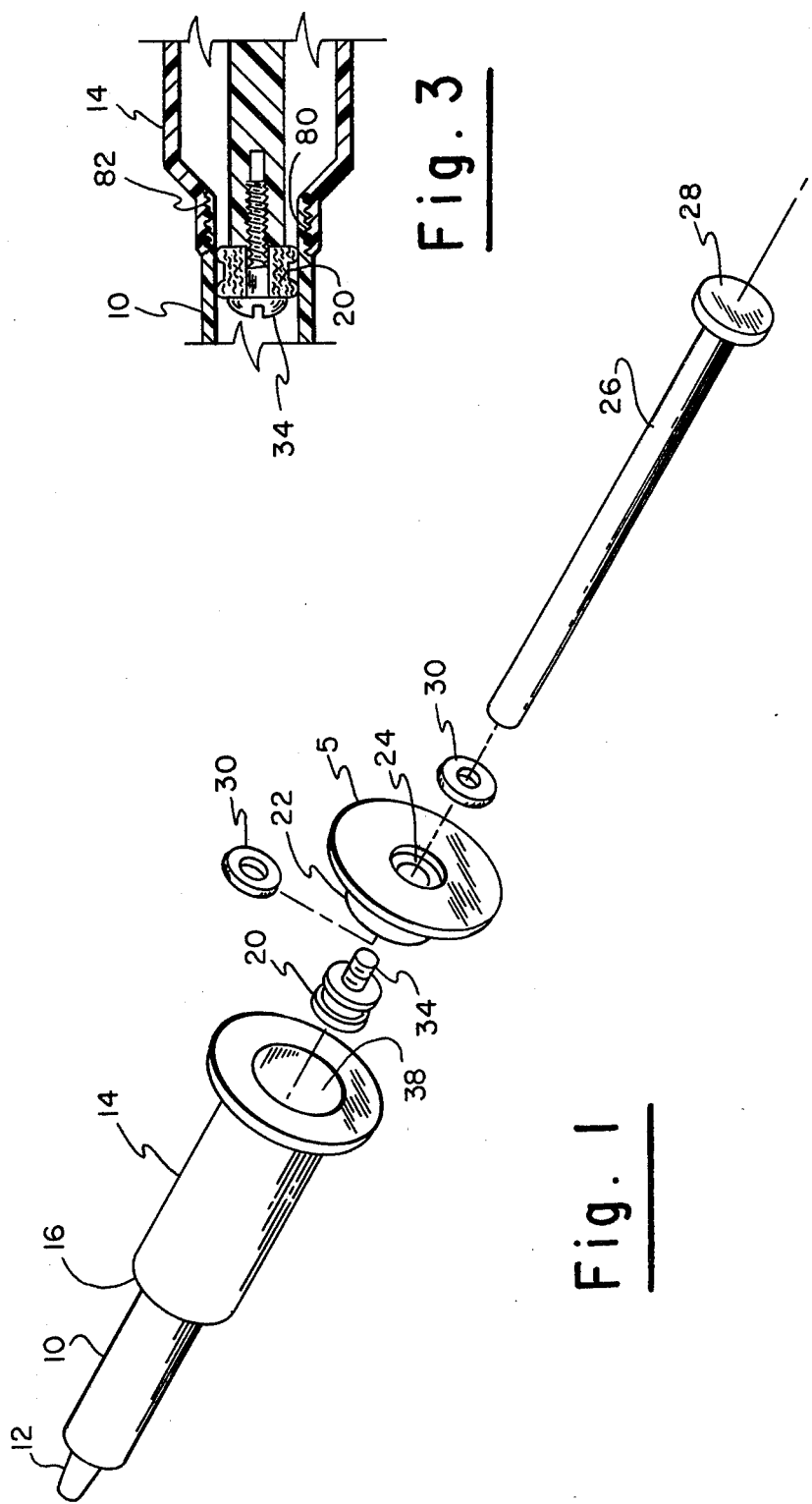
FIG. 1 is an exploded perspective view of the invention.
Figure 2:
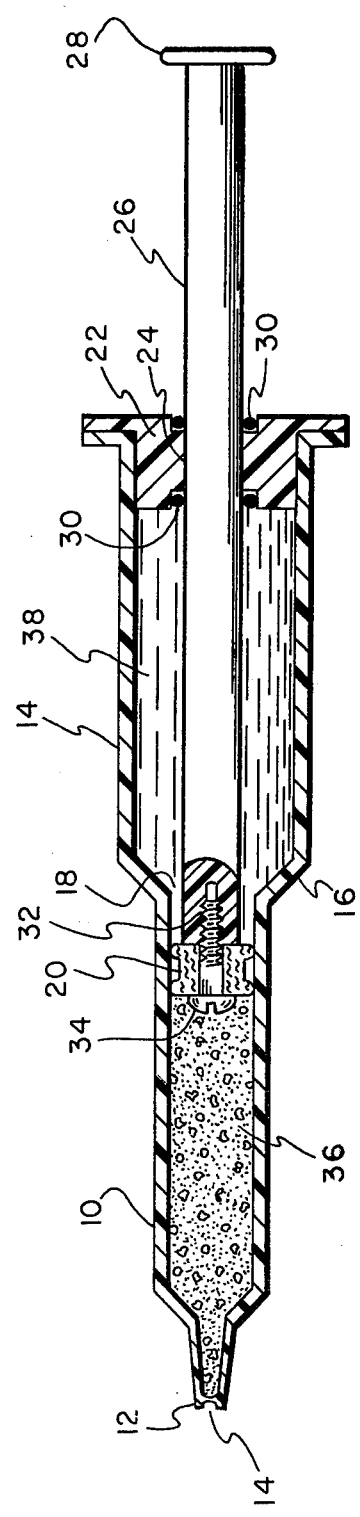
FIG. 2 is a longitudinal view in cross section of the structure shown in FIG. 1.

Referring now to the Figures, a first hollow elongated cylinder 10 has a first inner diameter, one end of the first cylinder being open, the opposite end of the first cylinder being closed and provided with a sealed tip 12 adapted to detachably receive a hypodermic needle.

A second hollow elongated cylinder 14 has a second and larger inner diameter, one end of the second cylinder being open, the opposite end of the second cylinder via having shoulder 16 with a circular port 18 with a diameter equal to the first diameter, centered therein. There cylinders are disposed end to end along a common cylindrical axis, the closed end of the second cylinder being secured to the open end of the first cylinder via shoulder 16 with said port being coincident with the open end of the first cylinder.

A sealing disc centered on said axis is slidable back and forth in said cylinders along said axis, said disc having a diameter equal to said first diameter and when disposed in said first cylinder engaging the inner surface thereof with a liquid tight seal.

A bushing 22 disposed in the open end of the second cylinder has a bore or circular opening 24 centered on said axis, said opening having a third diameter smaller than said first diameter.

An elongated cylindrical piston 26 extends slidably through said opening, there being a liquid tight seal between said piston and said bushing, one end 28 of said piston being disposed outside of the second cylinder and being enlarged, said piston being aligned with and centered on said axis, the length of the piston being longer than the combined lengths of said first and second cylinders.

O-rings 30 are disposed in the bore 24 between the bushing and piston to provide the desired liquid tight seal.

Cooperating detachably engagable means are on said disc and on the opposite end of the piston whereby said opposite piston end can be detachably secured to said disc.

More particularly the piston is manually rotatable about its axis and has a centrally disposed internally threaded bore 32 in the end adjacent disc 20. Disc 20 has a threaded screw 34 extending centrally and horizontally outward from the surface adjacent bore 32. When the piston is rotated in the clockwise direction with the bore 32 engaging the screw 34, the piston and disc will be engaged together and move as a unit. When the piston is rotated in reverse direction the piston and disc will separate. The disc is held in position by friction and will not rotate.

In use, the cylinder structure with bushing, piston and disc removed is held vertically, the internal portions of the structure being sterile, and lyophilized powder 36 is poured into the first cylinder. Using a sterile piston with sterile disc attached, the disc is inserted in the port and the piston is rotated to detach the piston from the disc. The diluent 38 is then poured into the second cylinder and the bushing, piston and seals are inserted. Tip 14 remains sealed.

When the syringe is to be used, the user moves the piston to engage the disc. The Piston is then pulled outwardly to pull the disc out of the port into the second cylinder, thus causing the diluent to pour into the first cylinder and mix with the powder.

A hypodermic needle can then be secured to the tip and caused to break the seal whereby the medicine can be injected as desired.

As shown in FIG. 3, the two cylinders can be detachably secured together as for example with cylinder 10 having an external thread 80 which engages the internal thread 82 on cylinder 14.

What is claimed is:

1. A medical syringe comprising:

a first hollow elongated cylinder having a first inner diameter, one end of the first cylinder being open, the opposite end of the first cylinder being closed and provided with sealed means adapted to detachably receive a hypodermic needle;

a second hollow elongated cylinder having a second and larger inner diameter, one end of the second cylinder being open, the opposite end of the second cylinder having centered therein a circular port with a diameter equal to the first diameter, said cylinders being disposed end to end along a common cylindrical axis, the opposite end of the second cylinder being secured to the open end of the first cylinder with said port being coincident with the open end of the first cylinder;

a sealing disc centered on said axis and being non rotatably slidable back and forth in said cylinders along said axis, said disc having a diameter equal to said first diameter and when disposed in said first cylinder engaging the inner surface thereof with a liquid tight seal, said disc having an axially aligned member having an external thread and extending toward said second cylinder;

a bushing disposed in the open end of the second cylinder and having a circular opening centered on said axis, said opening having a third diameter smaller than said first diameter, and an elongated cylindrical piston extending slidably through said opening, there being a liquid tight seal between said piston and said bushing, one end of said piston being disposed outside of the second cylinder and being enlarged, said piston being aligned with and centered on said axis, the length of the piston being longer than the combined lengths of said first and second cylinders, the other end of said cylinder having an axially disposed internally threaded bore which is engagable with said member when the piston is rotated in one direction about said axis and is disengagable from said member when the piston is rotated in opposite direction.

2. The syringe of claim 1 further including a liquid tight seal disposed in said opening between said bushing and said piston.

3. The syringe of claim 1 wherein said disc is disposed in said port, lyophilized powder is disposed in said first cylinder and diluent is disposed in said second cylinder.

* * * * *